United States Patent
Feinstein (10) Patent No.: US 10,455,900 B2
(45) Date of Patent: Oct. 29, 2019

(54) BI-STABLE STRAP WITH A SNAP SPRING HINGE

(71) Applicant: Peter A. Feinstein, Palm Beach Gardens, FL (US)

(72) Inventor: Peter A. Feinstein, Palm Beach Gardens, FL (US)

(73) Assignee: Feinstein Patents, LLC, Wilkes-Barre, PA (US)

( * ) Notice: Subject to any disclaimer, the term of this patent is extended or adjusted under 35 U.S.C. 154(b) by 0 days.

(21) Appl. No.: 15/599,200

(22) Filed: May 18, 2017

(65) Prior Publication Data

US 2018/0332928 A1    Nov. 22, 2018

(51) Int. Cl.
| | | |
|---|---|---|
| A44C 5/00 | (2006.01) |
| A43C 11/22 | (2006.01) |
| A61F 5/05 | (2006.01) |
| A61F 5/01 | (2006.01) |

(52) U.S. Cl.
CPC ............. *A43C 11/22* (2013.01); *A61F 5/0111* (2013.01); *A61F 5/05* (2013.01)

(58) Field of Classification Search
CPC ..................................................... A43C 11/22
See application file for complete search history.

(56) References Cited

U.S. PATENT DOCUMENTS

| | | | | |
|---|---|---|---|---|
| 5,325,613 A * | 7/1994 | Sussmann | ............... | A43C 11/00 24/712.2 |
| 5,791,021 A * | 8/1998 | James | ................... | A43C 1/003 24/68 SK |
| 5,794,360 A * | 8/1998 | Bell | .................... | A43C 11/1493 24/306 |
| 6,598,322 B2 | 7/2003 | Jacques et al. | | |
| 7,200,902 B2 * | 4/2007 | Browne | ............. | A44B 18/0003 24/442 |
| 7,308,738 B2 * | 12/2007 | Barvosa-Carter | ........................... | A44B 18/0003 24/442 |
| 7,600,301 B2 * | 10/2009 | Rudduck | ............... | F16B 1/0014 24/602 |
| 7,610,783 B2 * | 11/2009 | Rudduck | ................ | B62D 27/00 24/602 |
| 8,590,121 B1 * | 11/2013 | Patt, Jr. | ................ | A43B 3/0078 24/713.1 |

(Continued)

FOREIGN PATENT DOCUMENTS

| | | |
|---|---|---|
| EP | 1443834 B1 | 1/2007 |
| EP | 1952715 A1 | 8/2008 |

(Continued)

OTHER PUBLICATIONS

"An instant, custom-fitted shoe technology for the perfect footwear", Horizon 2020, The EU Framework Programme for Research and Innovation, Apr. 6, 2014, pp. 1-2.

(Continued)

*Primary Examiner* — Jason W San
(74) *Attorney, Agent, or Firm* — Forge IP, PLLC (57) ABSTRACT

A closure device including a beam, a catch at a distal end of the beam, a hinge connected to the beam, the hinge including a bi-stable spring and a shape memory element, and a controller connected to the shape memory element, the controller selectively delivering power to the shape memory element to change a state of the bi-stable spring.

13 Claims, 7 Drawing Sheets

(56) References Cited

U.S. PATENT DOCUMENTS

| | | |
|---|---|---|
| 8,935,860 B2 | 1/2015 | Torres |
| 9,307,804 B2 | 4/2016 | Beers et al. |
| 9,422,958 B2 * | 8/2016 | Vullings ............... F16B 5/0642 |
| 9,533,786 B1 | 1/2017 | Feinstein |
| 9,609,921 B1 | 4/2017 | Feinstein |
| 9,664,211 B2 * | 5/2017 | Tupper ................. F16B 1/0014 |
| 9,730,497 B2 * | 8/2017 | Huynh ..................... A44C 5/00 |
| 10,016,028 B2 * | 7/2018 | Shirasaka ............ A44C 5/0092 |
| 2015/0216252 A1 | 8/2015 | Wiens |
| 2015/0289594 A1 * | 10/2015 | Rushbrook ........... A43C 11/22 36/50.1 |
| 2015/0289596 A1 * | 10/2015 | Beers ..................... A43C 11/22 36/50.1 |
| 2016/0058128 A1 | 3/2016 | Dalton |
| 2016/0143397 A1 * | 5/2016 | Alvarez .................. A43C 1/00 24/441 |
| 2016/0309834 A1 | 10/2016 | Zwick et al. |
| 2017/0332736 A1 * | 11/2017 | Casas ................. A43C 11/1493 |

FOREIGN PATENT DOCUMENTS

| | | |
|---|---|---|
| WO | 03039283 A1 | 5/2003 |
| WO | 2010139456 A1 | 12/2010 |

OTHER PUBLICATIONS

"How Nike Built the Real Power-Lacing Shoe of Our Dreams", Scott Eden, Wired, Oct. 2016, pp. 1-24.

"Self-adjusting wearables: variable control through a shape-memory latching mechanism", UbiComp '16 Proceedings of the 2016 ACM International Joint Conference on Pervasive and Ubiquitous Computing: Adjunct, pp. 452-457 (abstract only) Sep. 12-16, 2016.

* cited by examiner

BI-STABLE STRAP WITH A SNAP SPRING HINGE

FIELD OF THE INVENTION

The invention relates generally to closure devices, and more particularly to a bi-stable strap with a snap spring hinge.

BACKGROUND OF THE INVENTION

There are many ways to close and tighten footwear and medical immobilization devices, such as orthopedic boots and casts. A similar situation applies to bands, such as watchbands. Closing and opening mechanisms are important to the workings of many products, and to inanimate objects such as packages, and boxes. Examples of conventional means include laces, ties, buckles, straps, tensioners, and Velcro. These generally require significant manual intervention or manipulation to close, tighten, and open. Depending on an individual's physical abilities or disabilities, this may vary from being an inconvenience to being impossible.

Efforts have been made to provide self-tightening closure devices. For example, there have been attempts to use shape memory materials to facilitate self-tightening closures in shoes and other devices. Shape memory materials generally change between an original state (e.g., baseline, memorized, permanent) and a deformed state (temporary shape) by means of an external stimulus. For example, a shape memory polymer can exhibit change from a rigid state to an elastic state, then back to the rigid state using an external stimulus. In similar respects, a shape memory alloy is an alloy that remembers its original shape and, after undergoing deformation, can transform back to its pre-deformed, original shape when triggered to do so.

U.S. Pat. No. 6,598,322 describes a shoe having an elongated shape memory alloy element and an electric circuit which when energized will produce a tightening of the shoe upper around the foot of a wearer. A battery contained in the shoe provides a power source to produce a current in the circuit that heats the shape memory alloy causing it to reduce its length providing the tightening of the shoe uppers. The circuit is energized by a switch in the shoe heel that is turned on by the wearer clicking his heels together. While the shape memory laces can be tightened and loosened without intervention, they remain tied which may lead to some difficulty in putting the shoes on and taking them off.

Another means of self-tightening a shoe is described in U.S. Pat. No. 8,935,860. This reference describes a shoe having a sole and a shoe upper, wherein the shoe is provided with a mechanism for automatically tightening the shoe on a foot to a preset level of tightness. The shoe includes a pressure sensor in the heel of the shoe along with a memory chip which stores a desired fit. Rather than using a shape memory material, the '860 patent tightens the several shoe straps using an electric motor powered by a battery.

While these references provide some assistance with tightening, they do not address the difficulty of latching and unlatching a closure device. Having laces, bands, or closures that only tighten and loosen without completely opening up may not be sufficient for some users, particularly during ingress and egress of a body part. It is desired to provide an improved solution and particularly a solution that substantially reduces or eliminates the necessity for manual intervention.

SUMMARY OF THE INVENTION

Accordingly, it is an object of the present invention to provide a closure mechanism including a bi-stable snap spring hinge actuated with a shape-memory alloy ("SMA"), shape memory polymer ("SMP"), or a combination of both types of materials. It is a further object of the present invention to provide such a mechanism that includes a magnetic clasp to facilitate the initial closure of the strap. It is a further object to provide articles, such as footwear, immobilization devices, watch bands, or any other applications requiring ingress or egress of body part, using such closures. The invention is not limited to such personal needs, and can be utilized for closure of, or enclosure around an object of any kind. Additional articles applicable to the present invention, as well as other features that may form part of the present invention, are provided in the inventor's own U.S. patent application Ser. Nos. 15/203,536 and 15/274,316 and U.S. Pat. Nos. 9,533,786 and 9,609,921. The contents of these applications and patents are incorporated herein by reference in their entirety.

These and other objectives are achieved by providing a closure device including a beam, a catch at a distal end of the beam, a hinge connected to the beam, the hinge including a bi-stable spring and a shape memory element, such as an SMA or SMP element, and a controller connected to the shape memory element, the controller selectively delivering power to the shape memory element to change a state of the bi-stable spring.

In some embodiments, actuation of the SMA/SMP changes the state of the bi-stable spring from a curved cross-section (straight length) state to a flat cross-section (bent length) state closing the closure device.

In some embodiments, the closure device includes a latch mechanism for release or opening, connectable to the catch, wherein at least one of the latch mechanism and the catch may include a magnet. The latch mechanism includes a motor and a gear screw that tightens the closure device. Lead screw forward motion is used to latch then tighten the strap by reducing the closed strap length. The strap is loosened via lead screw reverse motion.

In some embodiments, the shape memory element, such as an SMA or SMP element, is on an interior side of the hinge, wherein the hinge further includes a second shape memory element on an exterior side of the hinge, such that actuation of the second shape memory element changes the state of the bi-stable spring from a flat cross-section state to a curved cross-section state opening the closure device.

Other objects of the present invention are achieved by providing an immobilization device, including a cavity for receiving a body part or any object, including a first side and a second side adjustably movable with respect to one another, and at least one of the closure devices mounted between the first side and the second side. The device may be for example, an orthopedic boot or a cast. The immobilization device also includes a control unit including a microcontroller and a power supply, the control unit selectively delivering power to the shape memory element to change a state of the bi-stable spring from a curved cross-section state to a flat cross-section state thereby closing the at least one closure device.

Further provided is a watch, including a watch casing having a first side and a second side, and a watch band mounted between the first side and the second side. The watch band includes a first beam and a second beam, a catch at a distal end of the first beam, a latch mechanism at a distal end of the second beam, and at least one hinge connected to one of the first beam or the second beam, the hinge including a bi-stable spring and a shape memory element (alloy, polymer, or combination of both). The watch and watchband, and it's associated bi-stable strap with a snap spring hinge assembly, also has a control unit including a microcontroller and a power supply, the control unit selectively delivering power to the shape memory element to change a state of the bi-stable spring from a curved cross-section state to a flat cross-section state thereby closing the watch band.

Further provided is a footwear article, including a sole, an upper having a first side and a second side, and at least one closure device mounted between the first side and the second side. The at least one closure device includes a beam, a catch at a distal end of the beam, and a hinge connected to the beam, the hinge including a bi-stable spring and a shape memory element. A control unit is integrated in the footwear article, and/or in the associated bi-stable strap with a snap spring hinge assembly, including a microcontroller and a power supply, the control unit selectively delivering power to the shape memory element to change a state of the bi-stable spring from a curved cross-section state to a flat cross-section state thereby closing the at least one closure device.

Further provided is an object of any kind (animate or inanimate) requiring at least one closure device mounted between a first side and a second side. The at least one closure device includes a beam, a catch at a distal end of the beam, and a hinge connected to the beam, the hinge including a bi-stable spring and a shape memory element. A control unit is integrated into the object and/or the bi-stable strap with a snap spring hinge assembly including a microcontroller and a power supply, the control unit selectively delivering power to the shape memory element to change a state of the bi-stable spring from a curved cross-section state to a flat cross-section state thereby closing the at least one closure device.

Other objects of the invention and its particular features and advantages will become more apparent from consideration of the following drawings and accompanying detailed description.

DETAILED DESCRIPTION OF THE INVENTION

Figure 1:
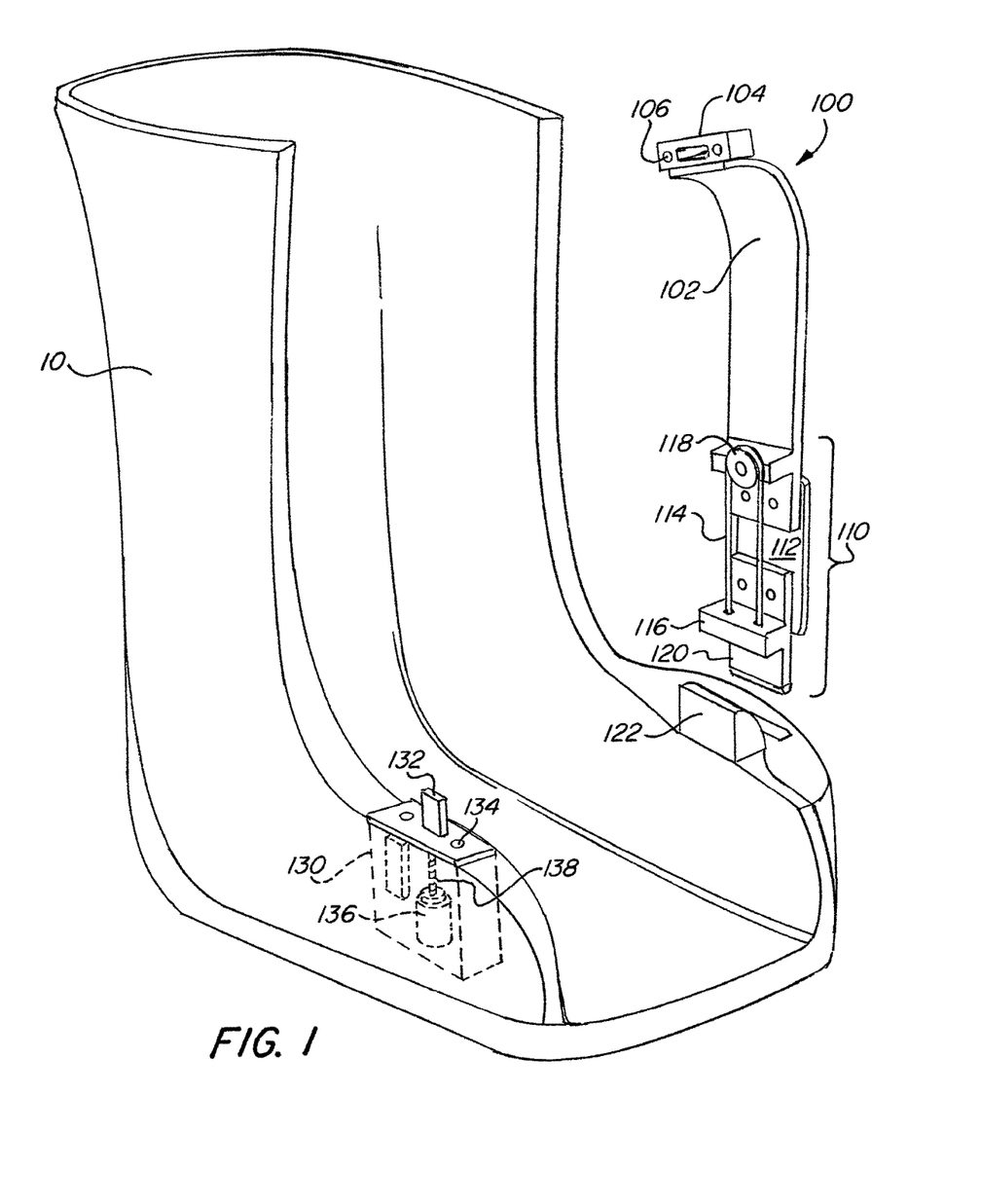
FIG. 1 illustrates an orthopedic boot with a closure device according to the present invention.

FIG. 1 illustrates a closure device or strap 100 according to the present invention on an orthopedic boot 10. FIG. 1 shows a single strap 100 on the boot 10; however, a plurality of straps 100, such as three, may be used. The strap 100 includes a formed beam 102, a bi-stable snap spring hinge 110, and a strap-boot interface 120. The beam 102 may be any shape or size and comprised of one or more rigid or soft materials. In some embodiments, the beam 102 is made of a thermoplastic or a carbon fiber. The beam 102 may also be adjustable in length.

The hinge 110 includes a bi-stable snap spring 112 and at least one shape memory element 114 that functions to actuate the spring 112. In the exemplary embodiment, the spring 112 is made of spring steel. The bi-stable spring 112 has two stable equilibrium states such as a first (open) state and a second (closed) state. In the first or open state (shown in FIG. 1), the spring 112 has a curved cross-section causing it to remain substantially straight or erect along its longitudinal axis or length. In the second or closed state, the spring 112 has a generally flat cross-section which allows the spring 112 to bend or curve along its length and no longer be straight. Actuation of the spring 112, by means of the SMA element 114, changes the spring 112 from one state to a second state, e.g., the curved cross-section state to the flat cross-section state.

The shape memory element 114 is comprised of a shape memory material such as an SMA, an SMP, or a combination of both types of materials. Suitable SMAs that may be used in the present invention include, but are not limited to, copper-aluminum-nickel alloys, nickel-titanium alloys, copper-zinc-aluminum alloys, iron-manganese-silicon alloys, gold-cadmium, brass, ferromagnetic, other iron-based alloys, and copper-based alloys. Suitable SMPs that may be used in the present invention include, but are not limited to, polyesters, polycarbonates, polyethers, polyamides, polyimides, polyacrylates, polyvinyls, polystyrenes, polyurethanes, polyethylene, polyether urethanes, polyetherimides, polymethacrylates, polyoxymethylene, poly-ϵ-caprolactone, polydioxanone, polyisoprene, styrene copolymer, styreneisoprene-butadiene block copolymer, cyanate ester, copolymers of stearyl acrylate and acrylic acid or methyl acrylate, norbonene or dimethaneoctahydronapthalene homopolymers or copolymers, malemide, silicones, natural rubbers, synthetic rubbers, and mixtures and compositions thereof. Further, the SMPs may be reinforced or unreinforced SMP material.

In the exemplary embodiment, the shape memory element 114 is comprised of nickel titanium, also known as Nitinol (e.g., 70C Nitinol). The shape memory element 114 is in the form of a string (e.g., 0.010-0.012 in. diameter, 3-5 ohms resistance per ten inches). The SMA element 114 is fixed to a base portion 116 of the hinge 110 and may extend around a pulley 118 on an opposite side of the hinge 110. In other embodiments, a pulley is not used. An approximately three (3) inch length of shape memory material is used between the base portion 116 and the pulley 118. Additional shape memory material may be needed to connect into a circuit, such as up to or approximately ten (10) inches of shape memory material.

The strap-boot interface 120 provides a means to connect the strap 100 to the article to be closed, such as the orthopedic boot 10. The interface 120 may be fixed or releasable. In the present embodiment, the interface is a buckle including a male buckle portion connected to the hinge 110 that is releasably received in a female buckle portion integrated in the boot 10.

The strap 100 further includes a latch catch 104 at or near a distal end of the beam 102. The catch 104 may be connected to or integrated into the tip of the beam 102. In some embodiments, the position of the latch catch 104 is adjustable in relation to the distal end of the beam 102. The catch 104 may include magnets 106 and/or hook features for interlocking with a latch mechanism 130 on an opposite site of the boot 10. In some embodiments, the strap 100 includes a clasp assembly as disclosed in the inventor's U.S. Pat. No. 9,609,921.

The latch mechanism 130 includes a latch 132 that is received by the catch 104 and, in some embodiments, magnets 134. The latch mechanism 130 may also include a gear motor 136 driving a lead screw 138 to tighten/tension the strap 100. The gear motor 136 is preferably an electric motor. The gear motor 136/lead screw 138 combination may include mechanisms that latch the strap 100 and unlatch/decouple the strap magnets prior to the strap 100 moving to the open position. In some embodiments, the latch mechanism 130 and/or lead screw 138 includes a spring to spring open the strap 100 into the open state.

Gear motor current may be monitored by the electronics system (including control unit 140 discussed below) to sense strap tightness. While tightening, gear motor current will increase and correspond to the force necessary to tighten the strap 100. When a desired tightness is reached, as determined by the current, tightening stops. In other embodiments, the strap 100 includes one or more sensors to provide signals to the control unit indicative of continuous tightness or pressure, or any other kind of sensing or input of data deemed to be of value in the functioning of the system. The sensors may be pressure sensors, or other types of sensors such as touch sensors, force sensors, capacitive sensors, conductivity sensors, light or optical sensors, heat sensors, strain gauges, stress gauges, bend sensors, magnetic sensors, location sensors, accelerometer sensors, mechanical sensors (e.g., external buttons or levels, removable tabs/rods/latches, external sliders, bending-release latches, etc.), or a combination thereof or any additional type of sensor.

Figure 2A:
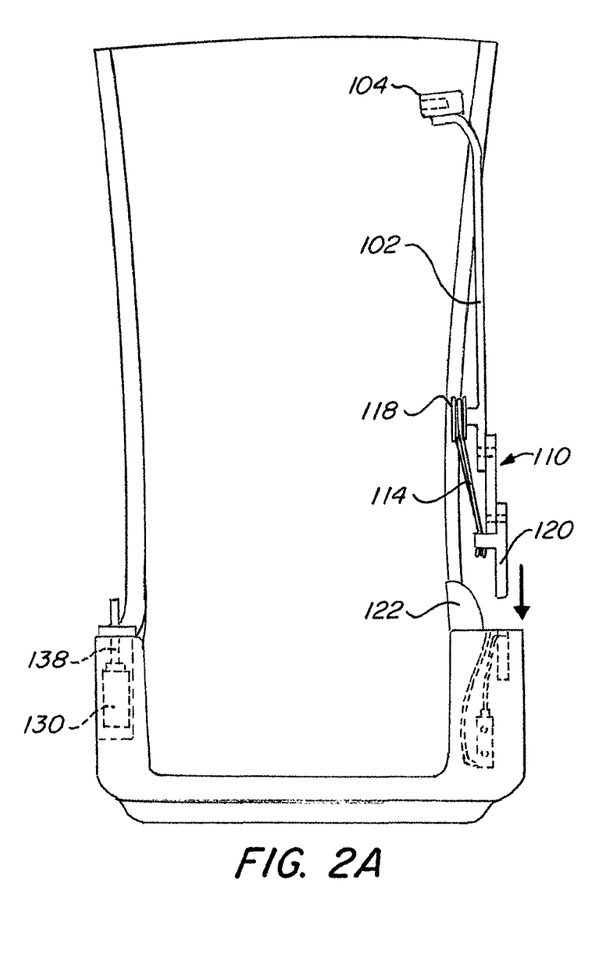
FIGS. 2A-2B illustrate the attachment and latching of the closure device shown in FIG. 1.
Figure 2B:
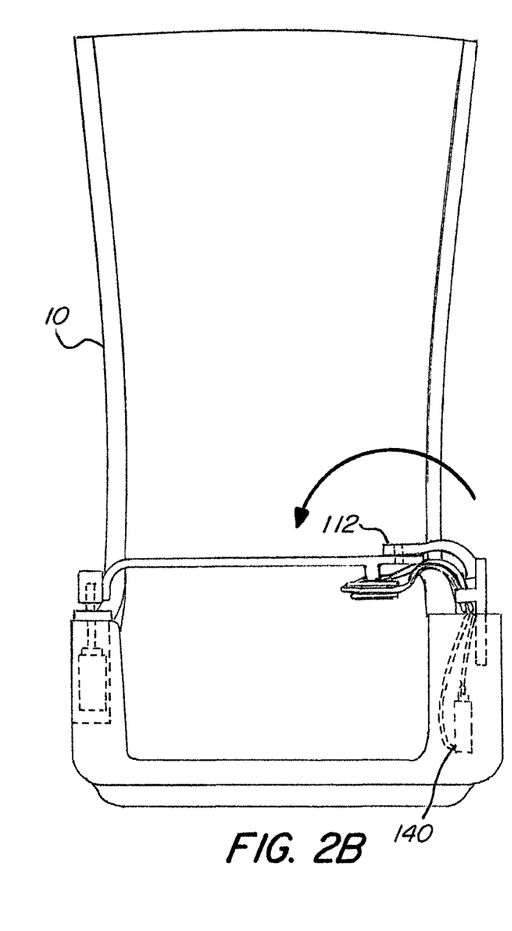

FIGS. 2A-2B illustrate the insertion, attachment and latching of the strap 100 of FIG. 1. The shape memory element 114 actuates the bi-stable spring 112 of the hinge 110 to swing the formed beam 102 into closed position for clasping across the orthopedic boot 10. Power is applied to the shape memory element 114 which reduces its length and actuates the hinge 110, i.e., moving the spring 112 from a curved cross-section (open) state (shown in FIG. 2A) to a flat cross-section (closed) state (shown in FIG. 2B) in which the spring 112 is flexible and can bend along its length. In one embodiment, the shape memory element 114 is reduced in length by 5% when power (e.g., 1 A, 5V) is applied. This pulls the bi-stable spring 112 from its curved cross-section and straight length state of FIG. 2A to its flat cross-section and bent length state of FIG. 2B, snapping the strap 100 into the closed position. Closing the strap 100 takes approximately one (1) second or less. The strap 100 utilizes a "normal bias spring" approach. The bend radius of the bi-stable spring 112 may be defined by a curved structural support or spring guide 122. As shown in FIGS. 2A-2B (and FIGS. 4-5), an electronics system including a control unit 140 is provided in communication with the shape memory element 114. The control unit 140 and associated components may be integrated in the boot 10 or directly in the strap 100.

The latch mechanism 130 receives the catch 104 to close the strap 100. In some embodiments, the latch mechanism 130 can also return the strap 100 to its open state. As discussed above, the latch mechanism 130 and/or lead screw 138 may include a spring to spring open the strap 100 into the open state. The spring may be integrated into the latch mechanism 130 in a way such that during the motion of the lead screw tightening the strap latch, the spring is compressed. Upon release of the lead screw 138 on the strap, the spring is released from its compressed state and pushes the strap 100 back into its open position.

Figure 3:
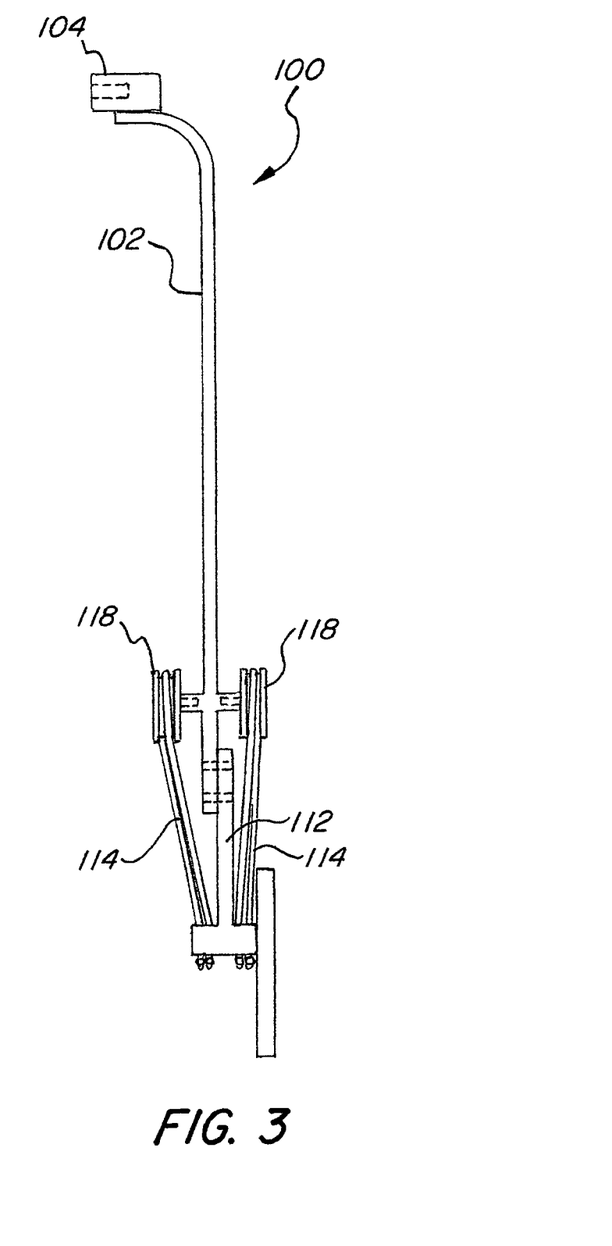
FIG. 3 illustrates another embodiment of the closure device shown in FIG. 1.

In some embodiments, the strap 100 has another length of shape memory material on opposite side of the spring 112. FIG. 3 illustrates another embodiment of the closure device shown in FIG. 1. In this embodiment, the strap 100 includes two shape memory elements 114, one on an interior side of the spring 112 and one on an exterior side of the spring 112. Actuation of the interior shape memory element 114 moves the strap into the closed position (e.g., FIG. 2B) and actuation of the exterior shape memory element 114 returns the spring 112 to its curved cross-section state (e.g., FIG. 2A) and opens the strap 100.

Figure 4:
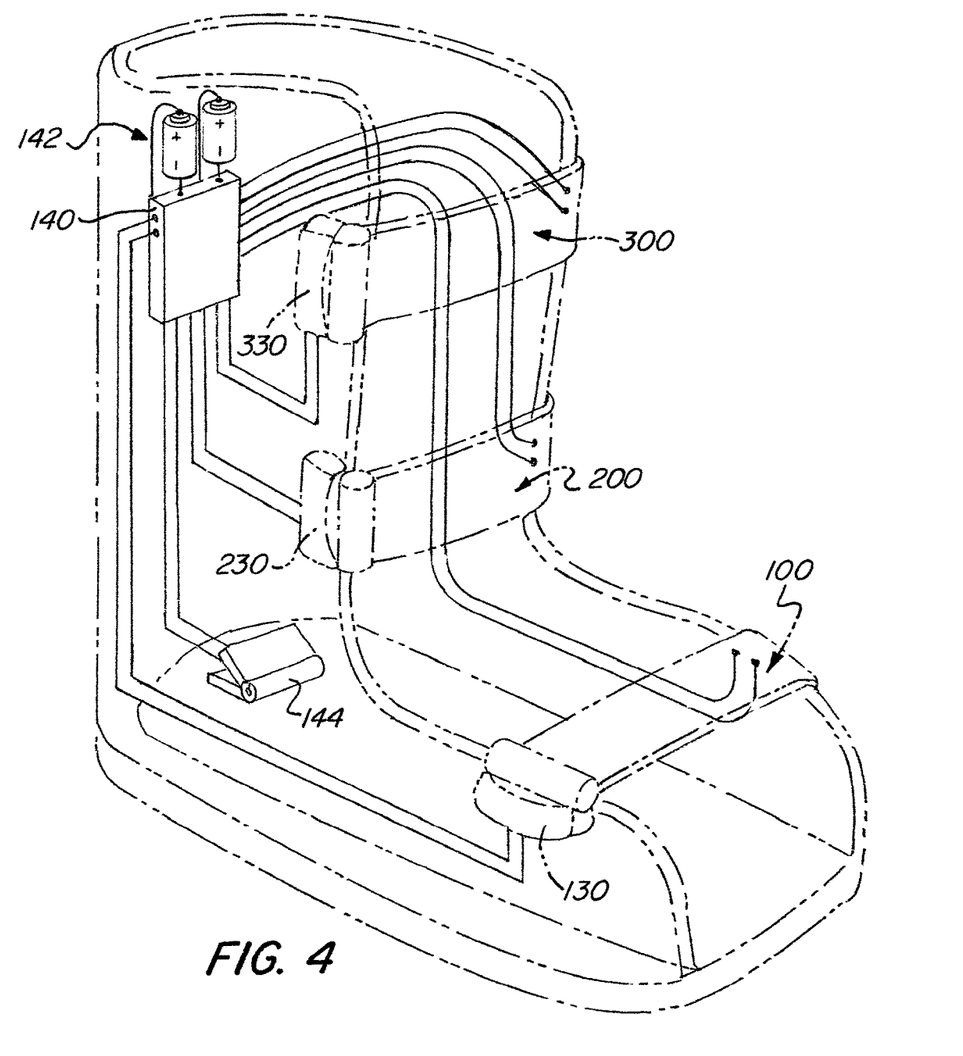
FIG. 4 illustrates an orthopedic boot including a plurality of closure devices according to the present invention.

FIG. 4 illustrates the orthopedic boot 10 having a plurality of the straps 100/200/300. In the present embodiment, the control unit 140 is housed in the back of the boot 10. The control unit 140 may be, or include components of, the control units described in the inventor's U.S. patent application Ser. Nos. 15/203,536 and 15/274,316. In the present embodiment, the control unit 140 includes a microcontroller on a printed circuit board (PCB) and a power supply 142 either internal to the control unit 140 or external thereto as shown, such one or more batteries (e.g., two CR123A batteries). To reduce the size of the power supply required, the straps 100/200/300 may actuate one-by-one rather than at the same time. In the exemplary embodiment, current is limited to 1.5 A at any given time. In other embodiments, each strap has its own electronics and power supply to eliminate wiring.

The control unit 140 may store and execute programmed feedback loops, algorithms, and artificial intelligence programs, and other mechanisms, to control tightness or looseness in real time. For example, the tightness may automatically adjust as described in the inventor's U.S. patent application Ser. No. 15/274,316. The control unit 140 and associated components comprising the electronics system may also include shape memory drive circuits, flexible circuitry, and wired connections to the shape memory element(s) 114, motor drive circuits and wired connection(s) to the gear motors 136, and connection(s) to a force sensor 144 to sense foot placed in the boot 10. The shape memory drive circuit(s) may include an NMOS transistor for turning power on/off for each shape memory wire. The motor drive circuit(s) may include an H bridge integrated circuit for each of the motors. In the exemplary embodiment, the foot sensor 144, such as a force sense resistor (FSR) or mechanical switch, is in the heel of the boot 10 and triggered when the user places their foot in the boot 10. This action signals the boot strap 100 to initiate a "move to close" sequence.

The straps 100 may be triggered to open by a signal. This may be in response to a user action, such as the press of a button on the boot 10 or by means of a remote user interface (e.g., push button on key chain, smart phone application) in wireless communication with the control unit 140. In some embodiments, the control unit 140 includes an accelerometer therein to generate the signal. For example, a specific foot motion or "gesture" could be sensed by the accelerometer to trigger the strap opening sequence. The accelerometer may be connected to the microprocessor via an SPI or I2C connection.

Figure 5:
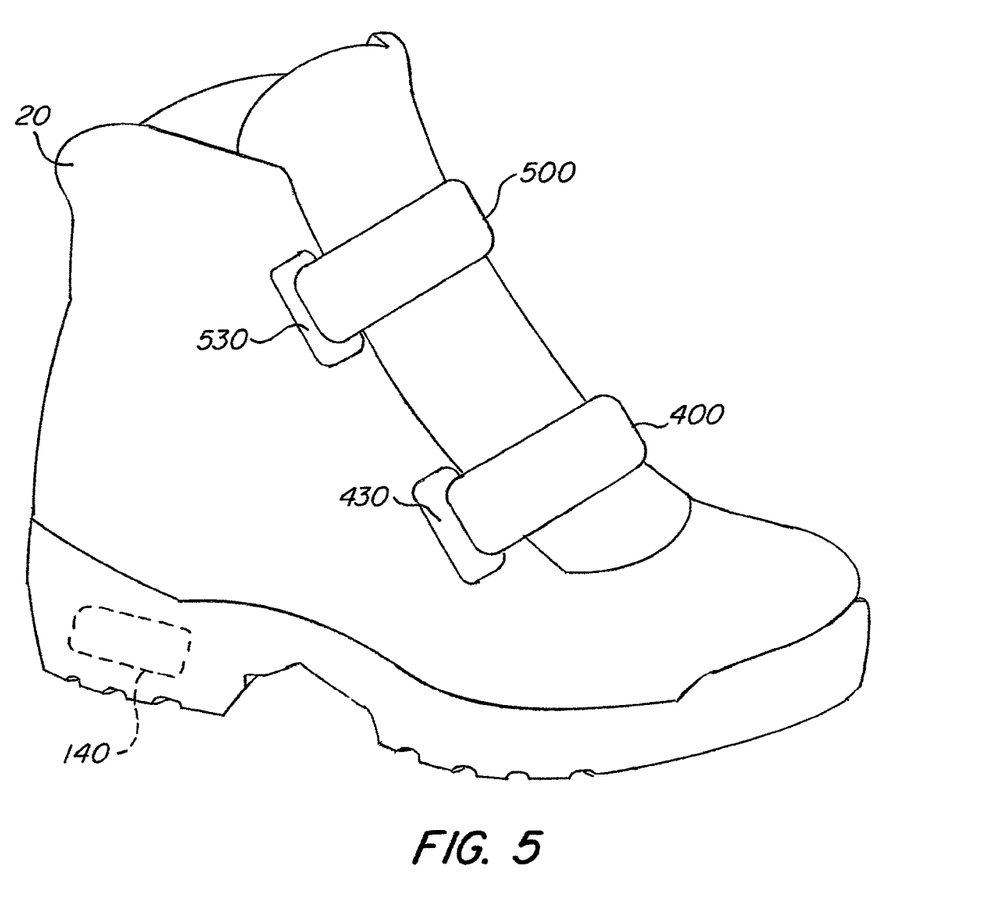
FIG. 5 illustrates a shoe including a plurality of closure devices according to the present invention.

The straps described above may be implemented in any type of article to be closed, such as orthopedic boots, casts, shoes, watches, packages, commercial products, etc. FIG. 5 shows a shoe 20 according to an exemplary embodiment of the present invention having a sole and an upper. The shoe 20 includes the straps 400/500 extending between first and second sides of the upper, latch mechanisms 430/530, and a control unit 140 (e.g., in the sole), the details of which are described above.

Figure 6A:
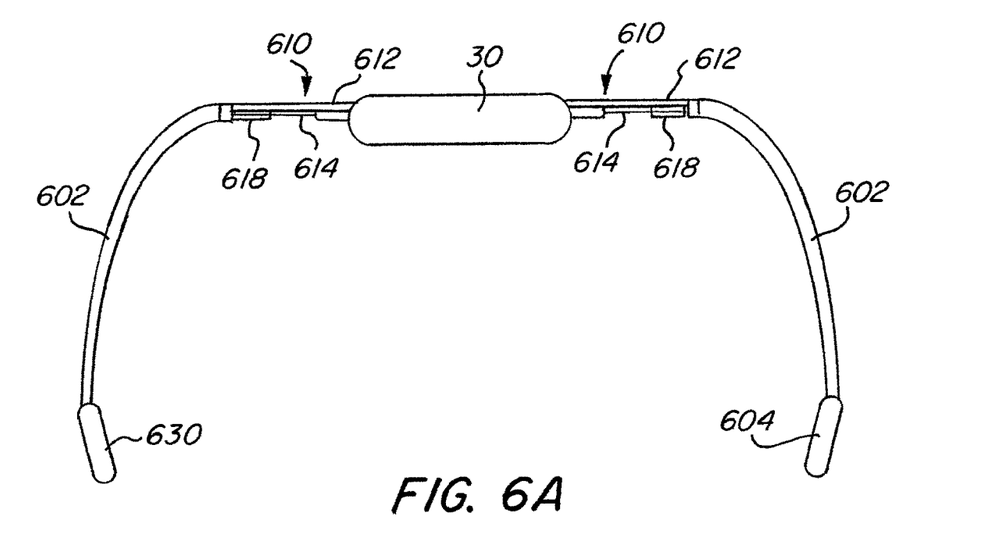
FIGS. 6A-6B illustrate a watch including a closure device according to the present invention.
Figure 6B:
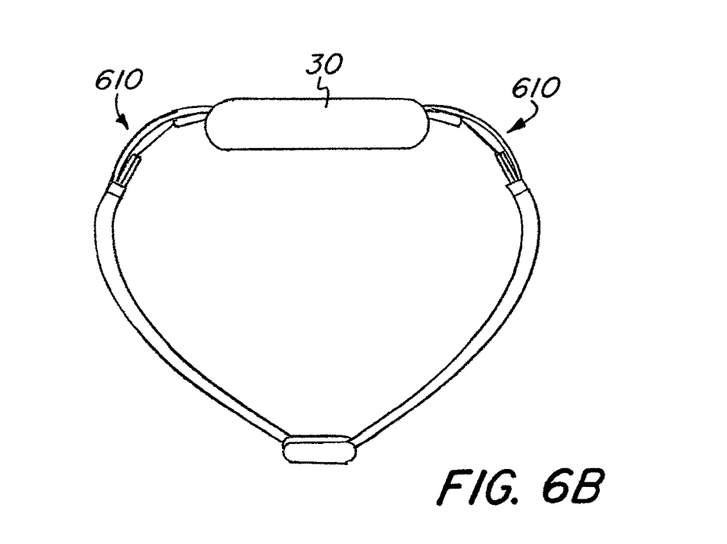

FIGS. 6A-6B shows a watch 30 according to an exemplary embodiment of the present invention. The watch 30 includes a closure device in the form of a watch band having two straps, each having a beam 602 and a bi-stable hinge 610 as described above. Each of the hinges has a spring 612, shape memory element 614, and optionally a pulley 618. A control unit of the watch 30 includes a microcontroller and power supply that actuates the shape memory elements 614. The control unit can be integrated within the watch casing and share components with the watch (e.g., such as the power supply). In other embodiments, the control unit is integrated in the straps. Upon actuating the shape memory elements 614, the watch band straps close around a user's wrist and the catch 604 receives the latch mechanism 630. In some embodiments, one or both of the catch 604 and the latch mechanism 630 include magnets to facilitate joining the two together.

Figure 7:
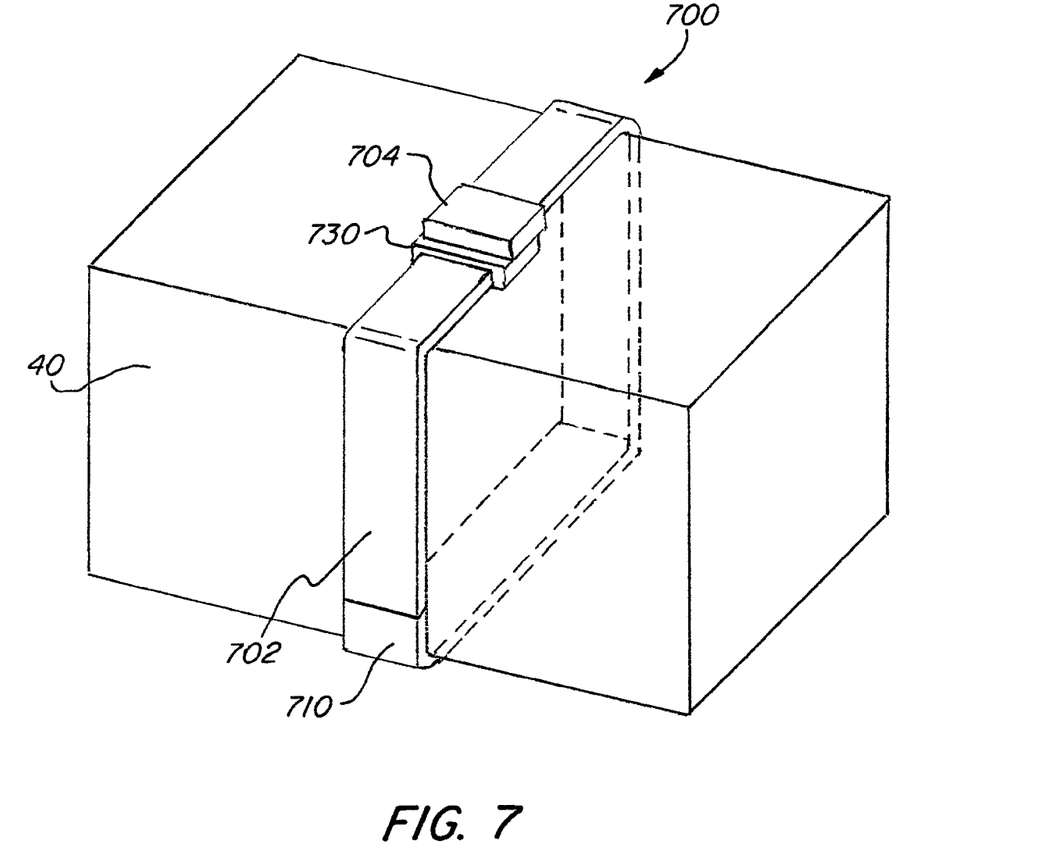
FIG. 7 illustrates an object including a closure device according to the present invention.

FIG. 7 illustrates an object 40 including a closure device 700 according to the present invention. The object 40 may be, for example, a package or anything else that is desired to be closed. The closure device 700 includes one or a plurality of hinges 710 having the features described above. The closure device also includes a beam 702, a latch catch 704, and a latch mechanism 730.

Although the invention has been described with reference to a particular arrangement of parts, features and the like, these are not intended to exhaust all possible arrangements or features, and indeed many modifications and variations will be ascertainable to those of skill in the art.

What is claimed is:

1. A closure device, comprising:
    a beam;
    a catch at a distal end of said beam;
    a hinge connected to said beam, said hinge including
        a bi-stable snap spring having a first state, in which the snap spring has a straight length with an arced width and a curved cross-section, and a second state, in which the snap spring has a bent length with a flat width and a flat cross-section;
        a shape memory element that changes the state of the bi-stable snap spring from the first state to the second state, the shape memory element having an original shape and a deformed shape; and
        a microcontroller connected to the shape memory element, wherein the shape memory element changes from the original shape to the deformed shape upon receiving power from the microcontroller such that the shape memory element snaps the bi-stable snap spring from the first state to the second state upon receiving the power.

2. The closure device of claim 1, said hinge including an interface for securing said closure device to an article to be closed.

3. The closure device of claim 2, wherein the article to be closed is one of a medical immobilization device, a footwear article, or a watch.

4. The closure device of claim 2, wherein the interface includes a male buckle portion connectable to a female buckle portion.

5. The closure device of claim 1, wherein the shape member element is an alloy, a polymer, or a combination thereof.

6. The closure device of claim 5, wherein the shape memory element is comprised of nickel titanium.

7. The closure device of claim 1, further comprising a latch mechanism releasable connectable to said catch.

8. The closure device of claim 7, wherein at least one of said latch mechanism and said catch including a magnet.

9. The closure device of claim 7, wherein said latch mechanism includes a motor and a gear screw that tightens the closure device.

10. The closure device of claim 9, wherein the gear screw includes a spring to push open the closure device upon release of the catch.

11. The closure device of claim 1, wherein the shape memory element is on an interior side of said hinge, wherein said hinge further comprises a second shape memory element on an exterior side of said hinge, wherein actuation of the second shape memory element changes the state of the bi-stable spring from a flat cross-section state to a curved cross-section state opening the closure device.

12. The closure device of claim 1, wherein the closure device is mounted to or at least partially around an object to be closed.

13. The closure device of claim 12, wherein actuation of the shape memory element changes the state of the bi-stable snap spring from an open state to a closed state, wherein in the closed state the closure device connects a first side of the object to a second side of the object.

* * * * *